United States Patent
Thompson, Jr. et al.

(10) Patent No.: US 10,016,289 B2
(45) Date of Patent: Jul. 10, 2018

(54) BIO-MECHANICAL PROSTHETIC THUMB

(71) Applicant: RCM ENTERPRISE LLC, Olympia, WA (US)

(72) Inventors: Robert Thompson, Jr., Olympia, WA (US); Jon Bengtsson, Olympia, WA (US); Charles Colin Macduff, Olympia, WA (US); Anthony Charles Peto, Olympia, WA (US); Sydney Tye Minnis, Seattle, WA (US); Eric Dennis Klumper, Boulder, CO (US); Bradley Arthur Crittenden, Olympia, WA (US)

(73) Assignee: RCM Enterprise LLC, Olympia, WA (US)

( * ) Notice: Subject to any disclaimer, the term of this patent is extended or adjusted under 35 U.S.C. 154(b) by 0 days.

(21) Appl. No.: 15/585,352

(22) Filed: May 3, 2017

(65) Prior Publication Data

US 2017/0296360 A1    Oct. 19, 2017

Related U.S. Application Data

(62) Division of application No. 15/247,611, filed on Aug. 25, 2016, now Pat. No. 9,713,541.

(Continued)

(51) Int. Cl.
*A61F 2/54* (2006.01)
*A61F 2/58* (2006.01)
(Continued)

(52) U.S. Cl.
CPC ............ *A61F 2/586* (2013.01); *A61F 2/5046* (2013.01); *A61F 2/68* (2013.01); *A61F 2/78* (2013.01);
(Continued)

(58) Field of Classification Search
CPC .... A61F 2/586; A61F 2/54; A61F 2002/7865; A61F 5/013
See application file for complete search history.

(56) References Cited

U.S. PATENT DOCUMENTS

| 319,776 A | 6/1885 | Bashore |
| 984,179 A | 2/1911 | Aydt |

(Continued)

FOREIGN PATENT DOCUMENTS

| GB | 2488365 | 8/1912 |
| GB | 110333 | 10/1917 |
| JP | 2002345861 | 12/2002 |

OTHER PUBLICATIONS

International Search Report and Written Opinion dated Nov. 4, 2016 for Int. Application No. PCT/US2016/048758, 7 pp.

(Continued)

*Primary Examiner* — Bruce E Snow
(74) *Attorney, Agent, or Firm* — James A. Sheridan; Sheridan Law, LLC

(57) ABSTRACT

There is disclosed a biomechanically driven prosthetic thumb assembly. Embodiments include an H-shaped rocker and a distal ring configured to receive a user's residual thumb, the distal ring and the rocker each independently and rotatively coupled between a coupling tip and a proximal anchor plate configured for affixing to a hand strap secured to a user. The coupling tip is articulated in response to a pulling force of the H-shaped rocker. Additional embodiments include a bidirectional thumb assembly including a ring mounted upon an adjustable ring tendon that is rotatively coupled between a coupling tip and a proximal anchor plate, which is rotatively coupled with a hand strap attached to the user. Vertical movement of the residual thumb within the ring actuates the coupling tip within a vertical plane.

(Continued)

Lateral movement of the residual thumb within the ring actuates the coupling tip within a lateral plane. Other embodiments are disclosed.

7 Claims, 13 Drawing Sheets

Related U.S. Application Data

(60) Provisional application No. 62/209,833, filed on Aug. 25, 2015.

(51) Int. Cl.
  *A61F 2/68* (2006.01)
  *A61F 2/78* (2006.01)
  *A61F 2/50* (2006.01)

(52) U.S. Cl.
  CPC .......... *A61F 2002/5001* (2013.01); *A61F 2002/5056* (2013.01); *A61F 2002/587* (2013.01); *A61F 2002/6872* (2013.01); *A61F 2002/7862* (2013.01)

(56) References Cited

U.S. PATENT DOCUMENTS

| | | | |
|---|---|---|---|
| 2,706,296 | A | 4/1955 | Fletcher |
| 2,867,819 | A | 1/1959 | George |
| 3,483,718 | A | 12/1969 | Lodrini |
| 3,707,963 | A | 1/1973 | Keropian |
| 4,258,441 | A | 3/1981 | Bell |
| 4,813,406 | A | 3/1989 | Ogle, II |
| 4,997,433 | A | 3/1991 | Goble et al. |
| 5,062,855 | A | 11/1991 | Rincoe |
| 5,941,914 | A | 8/1999 | Jacobsen et al. |
| 6,416,703 | B1 | 7/2002 | Kristinsson et al. |
| 6,908,489 | B2 | 6/2005 | Didrick |
| 8,337,568 | B2 | 12/2012 | Macduff |
| 9,375,319 | B2 | 6/2016 | Macduff |
| 2004/0054424 | A1 | 3/2004 | Matsuda |
| 2005/0043822 | A1 | 2/2005 | Didrick |
| 2006/0212129 | A1 | 9/2006 | Lake et al. |
| 2006/0224249 | A1 | 10/2006 | Winfrey |
| 2008/0127768 | A1 | 6/2008 | Shirai et al. |
| 2008/0262636 | A1 | 10/2008 | Puchhammer |
| 2010/0042229 | A1 | 2/2010 | Hawk |
| 2010/0082103 | A1 | 4/2010 | Blunn et al. |
| 2010/0191343 | A1 | 7/2010 | Puchammer et al. |
| 2010/0262057 | A1 | 10/2010 | Chandrasekhar et al. |
| 2011/0144770 | A1 | 6/2011 | Moyer et al. |
| 2011/0208322 | A1 | 8/2011 | Rifkin, Jr. et al. |
| 2012/0146352 | A1 | 6/2012 | Haslinger |
| 2012/0303136 | A1 | 11/2012 | Macduff |
| 2012/0330432 | A1 | 12/2012 | Fong |
| 2013/0226315 | A1 | 8/2013 | Varley |
| 2013/0268094 | A1 | 10/2013 | Van Wiemeersch |
| 2014/0078118 | A1 | 3/2014 | Robb |
| 2014/0202741 | A1 | 10/2014 | Macduff |
| 2014/0303749 | A1 | 10/2014 | Macduff |
| 2014/0303750 | A1 | 10/2014 | Macduff |
| 2014/0371897 | A1 | 12/2014 | Lin et al. |
| 2015/0138968 | A1 | 9/2015 | Hunter |

OTHER PUBLICATIONS

International Search Report and Written Opinion dated Aug. 26, 2016 for Int. Application No. PCT/US2016/032721, 20 pp.
International Search Report and Written Opinion dated Aug. 25, 2016 for Int. Application No. PCT/US2016/032732, 11 pp.
International Search Report and Written Opinion dated Jun. 10, 2016 for Int. Application No. PCT/US2016/016219, 6 pp.
Pop, S., "Finger Prosthetic Shows Perfect Balance Between Flexibility and Sturdiness—Gallery", Oct. 23, 2014, 9 pp.
International Search Report and Written Opinion dated Jun. 2, 2016 for Int. Application No. PCT/US2016/016223, 12 pp.
Leow, M., et al., "Optimal Circumference Reduction of Finger Models for Good Prosthetic Fit of a Thimble-Type Prosthesis for Distal Finger Amputations", Journal of Rehabilitation Research and Development, Mar. 2001, vol. 38, No. 2; pp. 273-279.
Cabibihan, J., "Patient-Specific Prosthetic Fingers by Remote Collaboration—a Case Study", PLoS One, May 2011, vol. 6, No. 5.
International Search Report and Written Opinion dated Apr. 22, 2016 for Int. Application No. PCT/US2016/016215, 8 pp.
Pop, S., "Finger Prosthetic Shows Perfect Balance Between Flexibility and Sturdiness—Gallery", Oct. 23, 2014, 8 pp. as downloaded on Jul. 12, 2017.

BIO-MECHANICAL PROSTHETIC THUMB

REFERENCE TO PENDING PRIOR PATENT APPLICATION

This application is a divisional of U.S. patent application Ser. No. 15/247,611, filed Aug. 25, 2016 by Robert Thompson Jr., Jon Bengtsson, Charles Colin Macduff, Anthony Charles Peto, Sydney Tye Minnis, Eric Dennis Klumper, and Bradley Arthur Crittenden for "BIO-MECHANICAL PROSTHETIC THUMB," which claims the benefit under 35 U.S.C. 119 (e) of U.S. Provisional Patent Application No. 62/209,833, filed Aug. 25, 2015 by Robert Thompson, Jon Bengtsson, Anthony Charles Peto, Sydney Tye Minnis, Eric Dennis Klumper, and Bradley Arthur Crittenden for "BIO-MECHANICAL PROSTHETIC THUMB," all of which patent applications are hereby incorporated herein by reference.

BACKGROUND

If a person loses a thumb, a thumb segment, or a thumb tip, the result is impaired performance of the hand. Having an amputated or partially amputated thumb inhibits the amputee from performing some of the most basic tasks. For example, with a lost thumb or thumb tip, the task of typing on a computer or simply dialing on a phone keypad becomes significantly difficult. These types of tasks require actions with precision that only thumbs are able to offer. Not only do thumbs allow people to perform precise actions, but the opposing nature of the thumb in relation to the remaining fingers provides the hand with an increased ability to lift and/or handle items. While holding an item in one hand, the weight of the item is dispersed throughout the user's thumb and fingers. By simply varying the force applied by the thumb on each of the holder's hands, the holder is able to manipulate the item(s) in a myriad of ways. However, if the holder is missing a single thumb or a portion of a single thumb, the amount of control available to manipulate the item(s) is dramatically decreased.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a prosthetic thumb assembly. The prosthetic thumb assembly may include (1) a coupling tip, (2) a distal ring configured to concentrically receive a residual thumb of a user, the distal ring having a first operable hinged connection with the coupling tip, (3) a proximal anchor plate having a second operable hinged connection with the distal ring, and an anchor attachment point configured for rotatively connecting the proximal anchor plate to the user, and (4) a rocker formed in an H-shape having a first end and a second end in opposition to one another, the first end forming a first split prong of the H-shape, the first end having a third operable hinged connection with the coupling tip, the second end forming a second split prong of the H-shape, the second end having a fourth operable hinged connection with the proximal anchor plate, where (a) the first and second operable hinged connections define a midline relative to a z-axis, (b) the third operable hinged connection is located below the midline, (c) the fourth operable hinged connection is located above the midline, and (d) the coupling tip is articulated in response to a pulling force provided by the rocker.

Another embodiment provides a biomechanically driven prosthetic thumb. The biomechanically driven prosthetic thumb may include (1) a coupling tip, (2) a proximal anchor plate configured for attachment to a hand strap, the hand strap configured for attachment about a hand of a user, (3) a distal ring having a body with an outer surface and an inner surface, the inner surface configured to concentrically receive a residual thumb of the user, and (4) an H-shaped rocker offset from the outer surface of the body of the distal ring, wherein the distal ring and the H-shaped rocker are independently and pivotally suspended between the coupling tip and the proximal anchor plate via a distal coordinated pivot point anchored upon the coupling tip and a proximal coordinated pivot point anchored upon the proximal anchor plate.

Yet another embodiment provides a bidirectional prosthetic thumb device. The bidirectional prosthetic thumb device may include an eccentric articulation pivot attached to a hand strap and an articulation assembly rotatively coupled with the eccentric articulation pivot. The articulation assembly may include a coupling tip, a proximal anchor plate, and an adjustable ring tendon having a distal end and a proximal end in opposition to one another, the distal end pivotally attached to the coupling tip and the proximal end pivotally attached to the proximal anchor plate. The articulation assembly may also include a ring configured to concentrically receive a residual thumb of a user, the ring in operable connection with the adjustable ring tendon, and selectively positionable at a target location between the distal end and the proximal end of the adjustable ring tendon. The articulation pivot may be configured to utilize abduction and adduction movements of the residual thumb within the ring to articulate the coupling tip within a plane parallel to an x-y plane and about an axis parallel to a z-axis, and the articulation assembly may be configured to utilize vertical movements of the residual thumb within the ring to articulate the coupling tip within a plane parallel to an x-z plane and about one or more axes parallel to a y axis.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments disclosed herein relate to a custom-designed, self-contained prosthetic thumb that may be fitted for a user with an amputated thumb, thumb tip, or thumb segment. The streamlined, sophisticated, and biomechanically driven design allows for a patient with any level of residual thumb to utilize a mechanical replacement that mimics the motions and functionalities of a real thumb. The natural action of the prosthetic thumb assembly allows users to regain maximum control of the flexion and extension movements of a full thumb and thumb tip and is designed to bend and curl in a realistic, natural manner in response to movement in the user's residual thumb, thumb joint, and/or adjacent fingers.

Embodiments described herein feature specially designed components, such as an H-shaped tendon or rocker and/or a cupped receiving tip, both discussed in detail below, that allow the prosthetic thumb to anchor to any length of residual thumb while protecting the amputation site against further injury or hypersensitivity and providing the individual user with maximum fit and use flexibility, dexterity, grip strength, and articulation.

Figure 1:
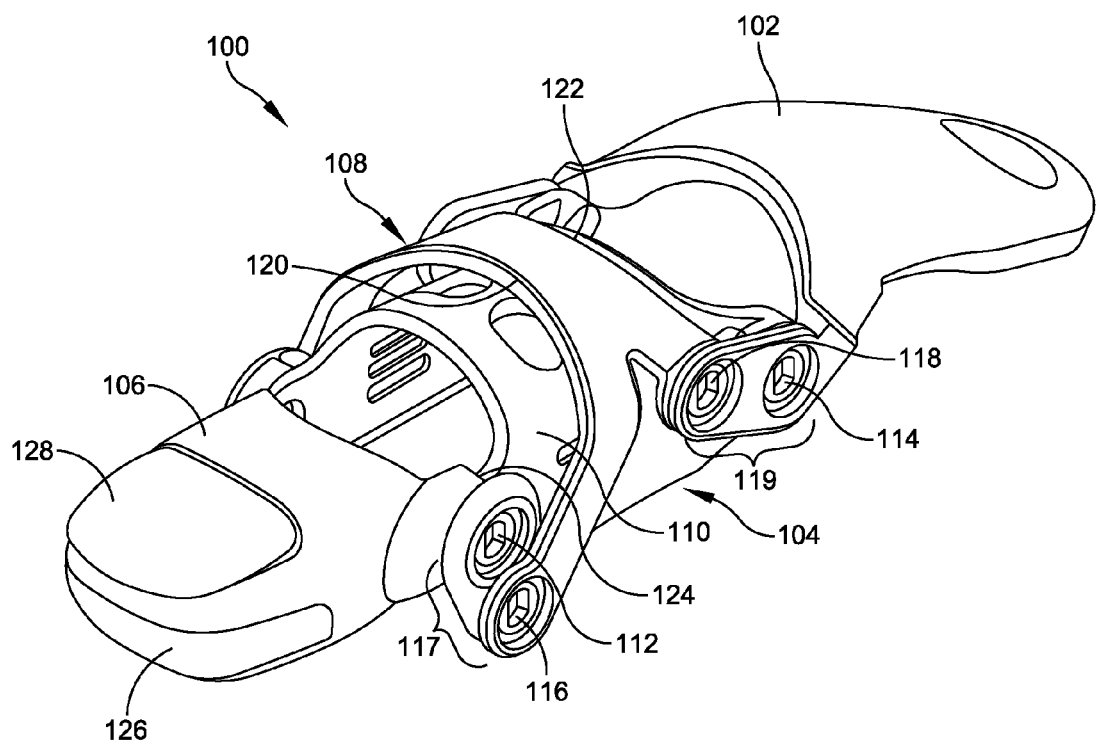
FIG. 1 illustrates a perspective view of one embodiment of a prosthetic thumb assembly.
Figure 2:
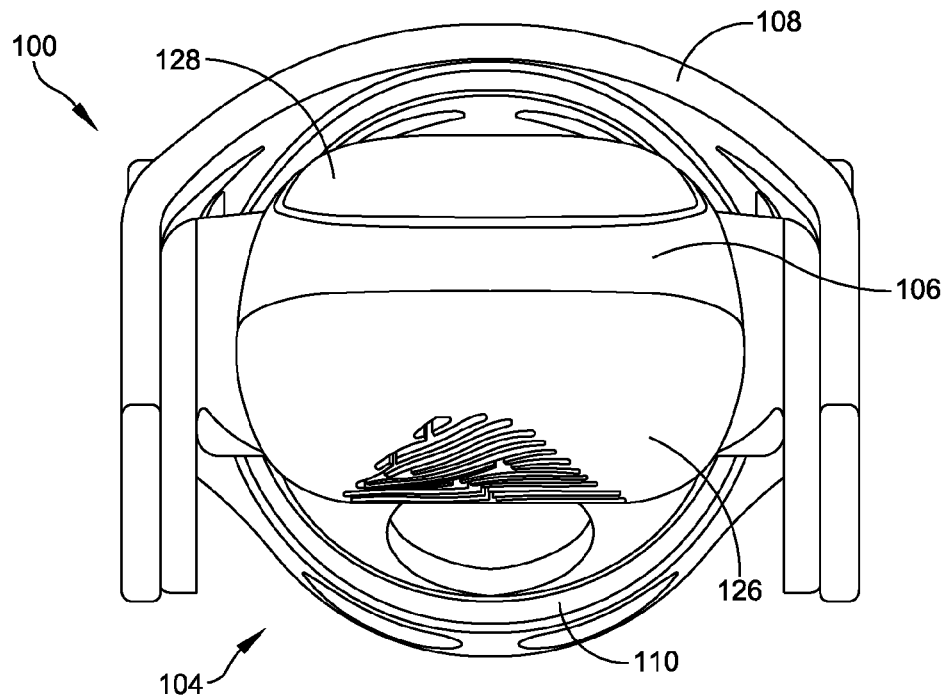
FIG. 2 illustrates a front view of the prosthetic thumb assembly of FIG. 1.
Figure 3:
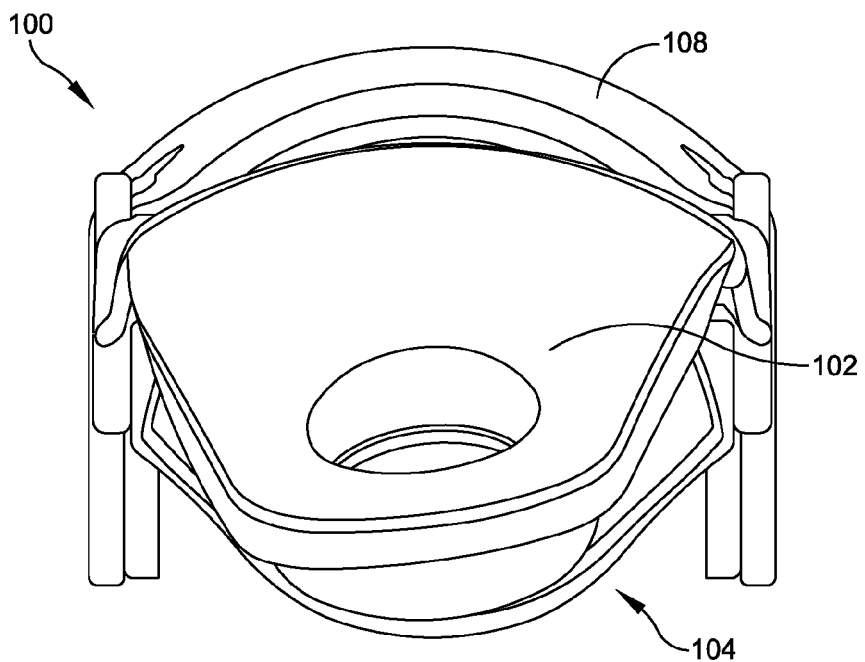
FIG. 3 illustrates a rear view of the prosthetic thumb assembly of FIG. 1.
Figure 4:
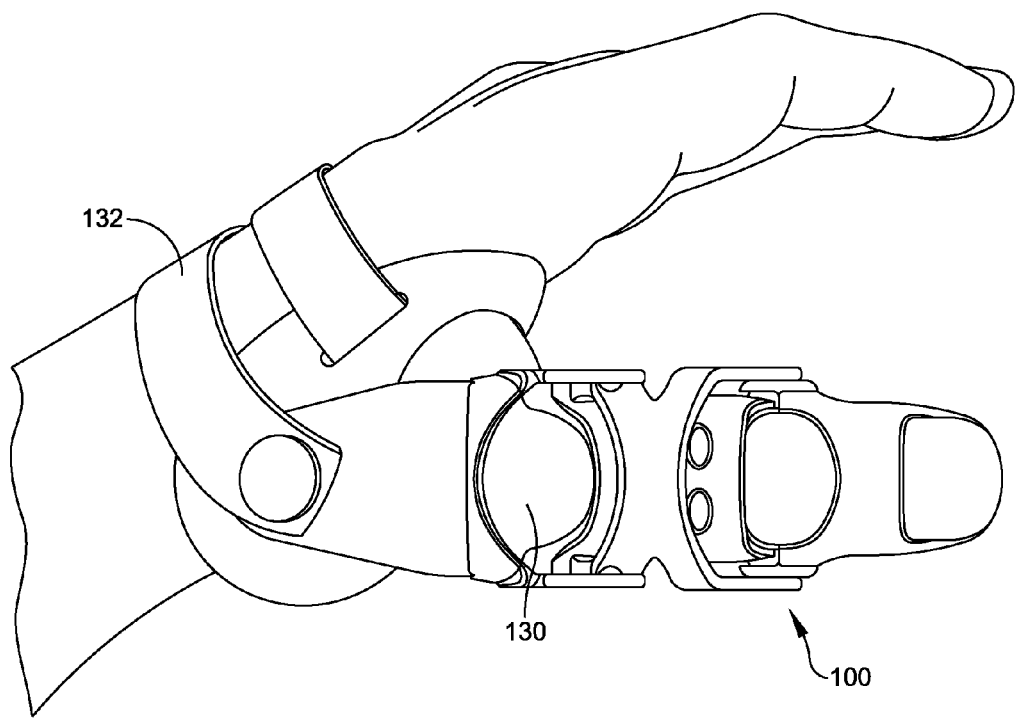
FIGS. 4-5 illustrate respective top and bottom perspective views of the prosthetic thumb assembly of FIG. 1, as attached to a hand of a user via a hand strap.
Figure 5:
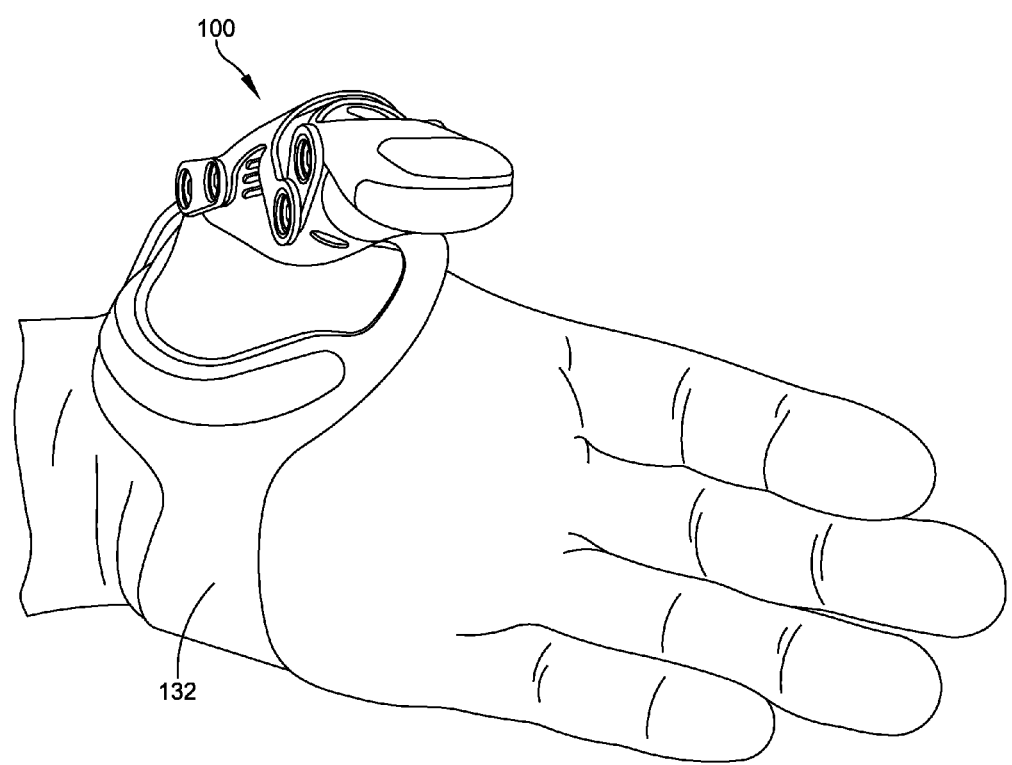

FIGS. 1-3 illustrate perspective, front, and rear views of one embodiment of a prosthetic thumb 100. In this embodiment, prosthetic thumb 100 may include four major interconnected components that extend from a proximal end located at the user's hand to a distal end located at a distance from the user's hand. These components include a proximal anchor plate 102, a distal ring 104, a coupling tip 106, and an H-shaped rocker 108. For installation purposes, distal ring 104 may have a body 110 that forms a ring shape that is designed to receive and encircle a user's residual thumb. More specifically, body 110 may be configured to anchor about a proximal phalange of a user's residual thumb with a snug fit. Proximal anchor plate 102 may be positioned above and anchored adjacent to the user's metacarpophalangeal (MCP) joint 130 using a hand strap 132, as shown in FIGS. 4-5. Embodiments of hand strap 132 may have any appropriate configuration necessary or appropriate to secure proximal anchor plate 102 in a proper position relative to the user's MCP joint 130, such that manipulation of the joint in relation to proximal anchor plate 102 actuates a number of hinged connections of prosthetic thumb 100.

Figure 6:
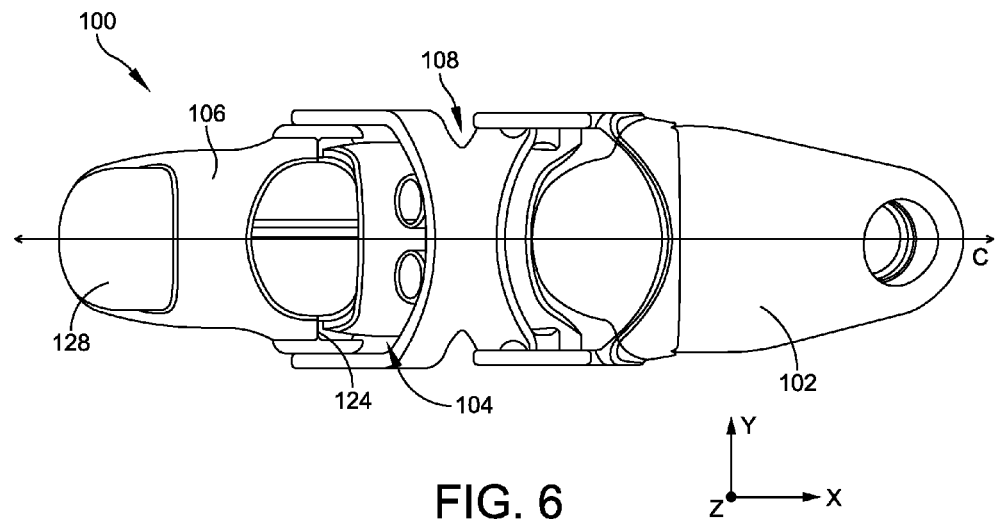
FIG. 6 illustrates a top view of the prosthetic thumb assembly of FIG. 1.

In further detail, a series of hinges may be used to secure the four primary components discussed above via rotative connections. In one embodiment, these rotative connections may be particularly positioned with respect to a pair of axes detailed in FIGS. 6-7. More specifically, FIG. 6 depicts a centerline, C, that bisects prosthetic thumb 100 relative to a y-axis, and FIG. 7 shows a midline, M, that intersects a first hinged connection 112 and a second hinged connection 114, both detailed below, relative to a z-axis.

Figure 7:
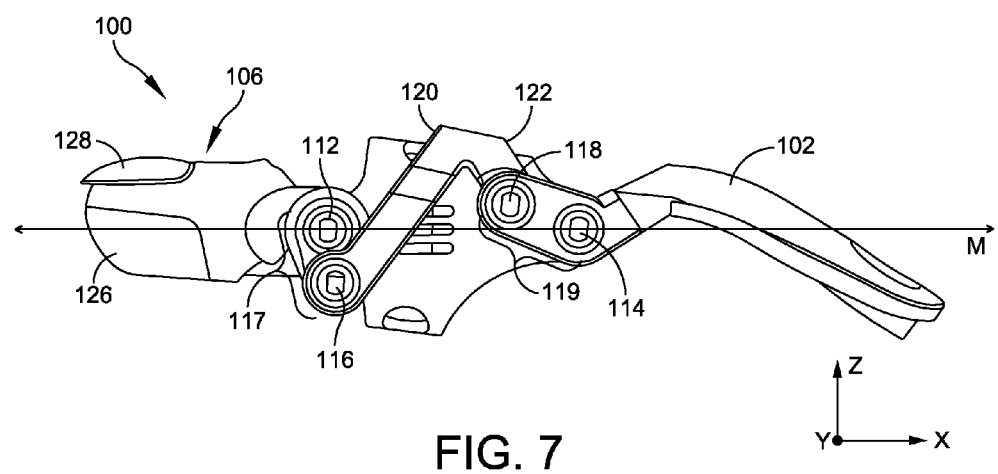
FIG. 7 illustrates a side view of the prosthetic thumb assembly of FIG. 1.

Turning to the various rotative connections detailed in FIGS. 1 and 7, distal ring 104 may rotatively couple with coupling tip 106 via first hinged connection 112. First hinged connection 112 may include a pair of parallel pivotal hinges that are symmetric about centerline, C, discussed above in relation to FIG. 6. Each of the pivotal hinges of first hinged connection 112 may provide a pivot point between distal ring 104 and coupling tip 106.

Distal ring 104 may rotatively couple with proximal anchor plate 102 via second hinged connection 114. Second hinged connection 114 may also include a pair of parallel pivotal hinges that are symmetric about the centerline, C, one located on each side of prosthetic thumb such that each provides a pivot point between distal ring 104 and coupling tip 106. As discussed above in relation to FIG. 7, the midline, M, intersects first and second hinged connections 112, 114, and therefore, both first and second hinged connections 112, 114 are located directly upon the midline, M, relative to the z-axis.

Rocker 108 may form an H-shape having opposing first and second ends 120, 122, respectively, that extend between coupling tip 106 and proximal anchor plate 102. First end 120 may form a first split prong of the H-shape, which may rotatively couple with coupling tip 106 via a third hinged connection 116 located below the midline, M, relative to the z-axis (FIG. 7). Second end 122 of rocker 108 may form a second split prong of the H-shape, which may rotatively couple with proximal anchor plate 102 via a fourth hinged connection 118 located above the midline, M, relative to the z-axis (FIG. 7). Each of third and fourth hinged connections 116, 118 may include a pair of parallel pivotal hinges that are symmetric about the centerline, C, each providing a respective pivot point between rocker 108 and coupling tip 106 at the first end 120 and proximal anchor plate 102 at the second end 122.

Any one or more of the first, second, third, and/or fourth hinged connections 112, 114, 116, 118 may feature a hard-stop to prevent hyperextension of prosthetic thumb 100 during operation. For example, a hard-stop 124, shown in FIGS. 1 and 6, may prevent relative over-rotation of first hinged connection 112, or between coupling tip 106 and distal ring 104. Mechanical hard-stops may have any appropriate size, shape, and/or configuration.

In this embodiment, first and third hinged connections 112, 116 may align to form a distal coordinated pivot point 117, which is anchored upon coupling tip 106. Similarly, second and fourth hinged connections 114, 118 may align to form a proximal coordinated pivot point 119, which is anchored upon proximal anchor plate 102. While distal ring 104 and H-shaped rocker 108 do not directly connect with one another, each directly and pivotally connects with coupling tip 106 and proximal anchor plate 102 via the distal and proximal coordinated pivot points 117, 119, respectively. As a result, rocker 108 and distal ring 104 are each independently, pivotally suspended between coupling tip 106 and proximal anchor plate 102, such that they articulate in coordinated, yet independent, manners relative to one another and about numerous axes parallel to the y-axis. This association of rocker 108 and distal ring 104, without an actual direct link or connection between the two components, allows for complex, realistic vertical articulation motions (e.g., motions within planes parallel to the x-z plane) of coupling tip 106 in response to biomechanical input forces exerted by the residual thumb on proximal anchor plate 102 and distal ring 104.

Working together, proximal anchor plate 102, distal ring 104, coupling tip 106, and rocker 108 form a 4-bar linkage system that allows coupling tip 106 to be articulated in response to a pulling force on distal ring 104, much like the working framework of tendons within the human hand. In this regard, the linkage created by hinged connections 112, 114, 116, and 118 allow both distal ring 104 and H-shaped rocker 108 to be independently and rotatively suspended between coupling tip 106 and proximal anchor plate 102. While distal ring 104 is rotatively connected between coupling tip 106 and proximal anchor plate 102 through first and second hinged connections 112 and 114, and while rocker 108 is rotatively connected between coupling tip 106 and proximal anchor plate 102 through third and fourth hinged connections 116 and 118, respectively, distal ring 104 and rocker 108 are not directly connected. This allows for complementary, yet independent movement of each of distal ring 104 and rocker 108 in relation to one another. Both parts move in response to movement of the user's residual thumb within distal ring 104 and/or movement of the user's MCP joint beneath proximal anchor plate 102, and the nature of the indirect connection between the two components provides for complex, reactive motions to pulling forces provided the hand, thereby enabling thumb 100 to emulate natural movements.

The pulling force applied either by the residual thumb or by the MCP joint places the distal ring 104 in tension and reduces the risk of buckling. Thus, natural movement of the patient's residual thumb seated within distal ring 104, or in some cases movement of the MCP joint and/or the adjacent fingers, may be used to actuate realistic flexion and extension motions within prosthetic thumb 100. Users may perform their full range of usual activities, including typing, playing a musical instrument, lifting and manipulating intricate and/or awkward objects, and any other activities that require the full dexterity of the hand.

The H-shape of rocker 108 allows third hinged connection 116 between rocker 108 and coupling tip 106 to occur outside the assembly of thumb 100, or outside the physical boundary defined by distal ring 104 and coupling tip 106. This configuration allows users with a relatively longer residual thumb, or a relatively long proximal phalanx, to take advantage of additional clearance space within the assembly. Residual thumbs of varying lengths may fit comfortably within the assembly, while still being protected against further damage and/or hypersensitivity. That said, while rocker 108 is described herein as having an H-shaped profile, it should be understood that rocker 108 may take any appropriate size, shape, type, and/or configuration.

Embodiments of prosthetic thumb 100 are custom designed and individually fitted to accommodate a variety of differing user conditions, including different residual-thumb lengths (e.g., varying amounts of loss to the thumb). In this regard, each thumb 100 may be customized to fit a particular patient or user, providing both custom functionality as well as a mechanical match to the anatomical joint articulation of the particular user, including matching the length of the original, non-amputated thumb. Design considerations include an amount of thumb loss, a number of joints to be replaced, and other characteristics specific to the individual end user.

H-shaped rocker 108 is designed to provide a full-coverage "cage" above and about a patient's residual thumb, thereby protecting the residual thumb from irritation and/or hypersensitivity, without interfering with the residual thumb within the prosthetic device 100. Outfitted with H-shaped rocker 108, a user may anchor any length of residual thumb within prosthetic thumb 100, even if the residual thumb length extends past the interphalangeal joint. In cases in which the user has a fully formed, but poorly or nonfunctioning thumb, coupling tip 106 may be removed so that prosthetic thumb 100 may function as a joint brace, rather than a digit replacement. Alternatively, coupling tip 106 may include a cup or a recess that is adapted to receive all or a portion of the thumb tip in instances in which the patient has experienced little or no digit loss, but who does not have a fully functioning thumb.

In the embodiment shown in FIGS. 1-8, coupling tip 106 may include a tip pad 126. Tip pad 126 may be formed from a soft-textured silicone or other material that mimics the texture of a real thumb tip. This aids with gripping and provides a softer touch. In one embodiment, a touchscreen mechanism (not shown) may be provided to allow the user to use prosthetic thumb 100 to operate capacitive touchscreens, which react to the body's natural electrical current. The touchscreen mechanism allows the user to direct his or her own body current through the tip of the prosthetic thumb.

One embodiment of coupling tip 106 may also include a thumbnail 128, which mimics a natural edged nail that may provide scratching and peeling functionalities as well as assist with fine-object manipulation.

To further provide better aesthetics, embodiments of thumb 100 may be coated with films and/or colorings matched to the user's skin tone. An additive manufacturing process (i.e., 3D printing) facilitates this ability to customize the intricacies of the prosthetic thumb design in order to optimize prosthetic thumb 100 for each user.

Embodiments of prosthetic thumb 100 may be formed of any suitable structural material that is non-irritating to human skin and allows the user to operate the prosthetic with comfort and confidence. Exemplary materials include titanium, stainless steel, aluminum, silicone, carbon fiber, nylon, plastic/polymer, wood, rubber, gold, silver, tungsten, flex cable, neoprene, or any other suitable material. In one embodiment, components of prosthetic thumb 100 are 3D printed from Duraform EX polymer material.

Using biocompatible materials, various embodiments of prosthetic thumb 100 may be applied as an orthopedic implant that may be surgically implanted into a user's thumb. This option may be applied for users having injuries that have crushed their finger bones without the ability to heal or be repaired. In these situations, implantable embodiments of prosthetic thumb 100 are able to take the place of the user's original bones without the need for amputation.

Figure 8:
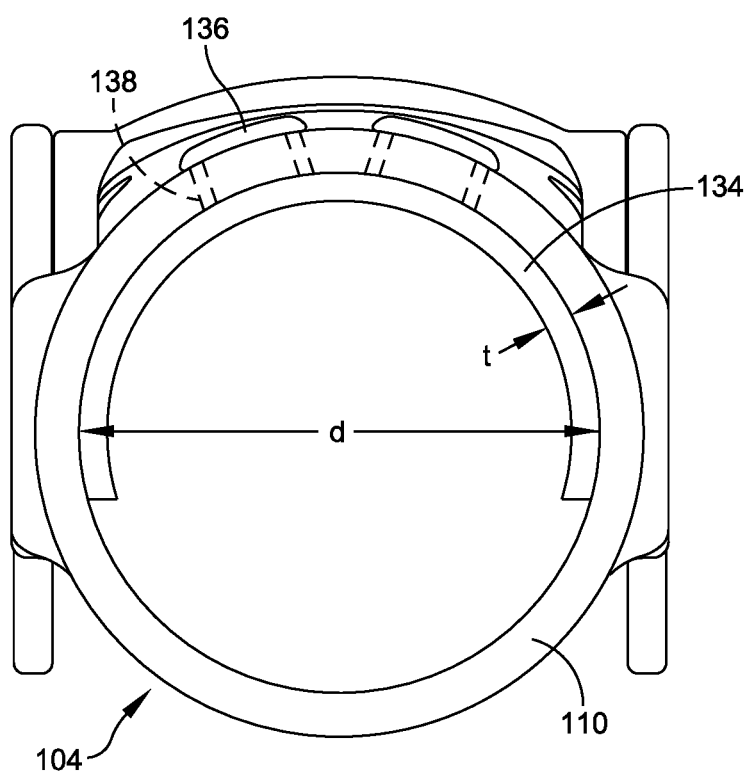
FIG. 8 illustrates a rear view of the prosthetic thumb assembly of FIG. 1, with a proximal anchor plate removed.

To use, the user may simply slide distal ring 104 onto his or her residual thumb and secure proximal anchor plate 102 above/adjacent to the user's MCP joint 130 using hand strap 132 (FIGS. 4-5). If necessary, distal ring 104 may be further adjusted or tailored for the user via a number of sizing shims. FIG. 8 illustrates a rear view of prosthetic thumb 100, with proximal anchor plate detached from the remaining assembly. In this embodiment, distal ring 104 has been outfitted with a semi-circular shim 134, which may be inserted into an interior of distal ring 104 to allow the sizing of body 110 to be adjusted incrementally for weight gain/loss, swelling, and/or other post-manufacture changes in the diameter of the user's residual thumb. In further detail, a fit kit (not shown) may be provided with each prosthetic thumb 100 and may include a number of shims 134. In one embodiment, each shim 134 may approximate a semi-circle or U-shape configured to abut an inner diameter, d, of body 110 of distal ring 104 and may have a number of retaining grommets 136 configured to protrude through corresponding shim-retainment apertures 138 within body 110. Each shim 132 may have a different thickness, t, thereby allowing the user to adjust the inner diameter, d, of body 110 of distal ring 104 in a number of increments as required by the user.

Once prosthetic thumb 100 is adjusted and in place, the user may utilize his or her natural movements of the residual thumb and/or MCP joint. The primary components of prosthetic thumb 100 will articulate using the same cognitive process that was previously used for the original thumb.

Figure 9:
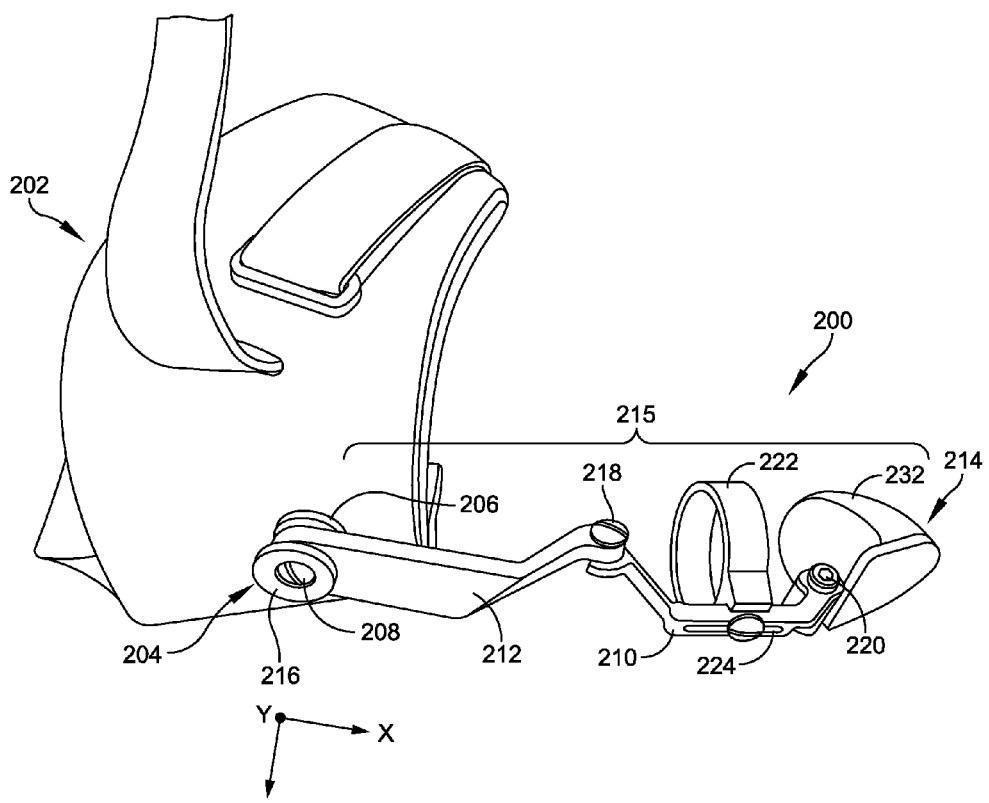
FIG. 9 illustrates a perspective view of an alternative prosthetic thumb assembly and corresponding hand strap.
Figure 10:
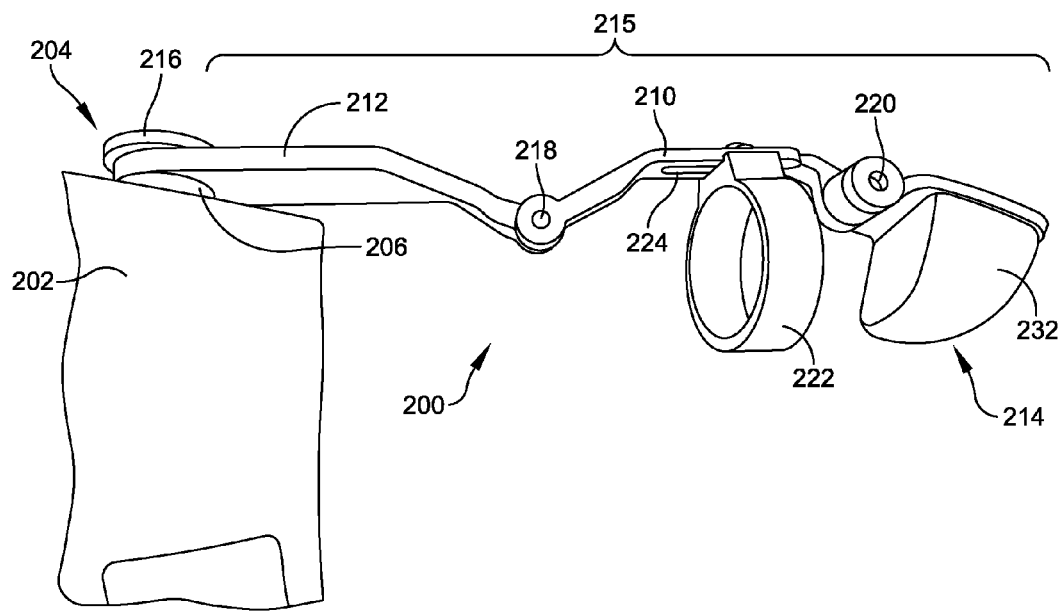
FIG. 10 illustrates another perspective view of the prosthetic thumb assembly of FIG. 9.
Figure 11:
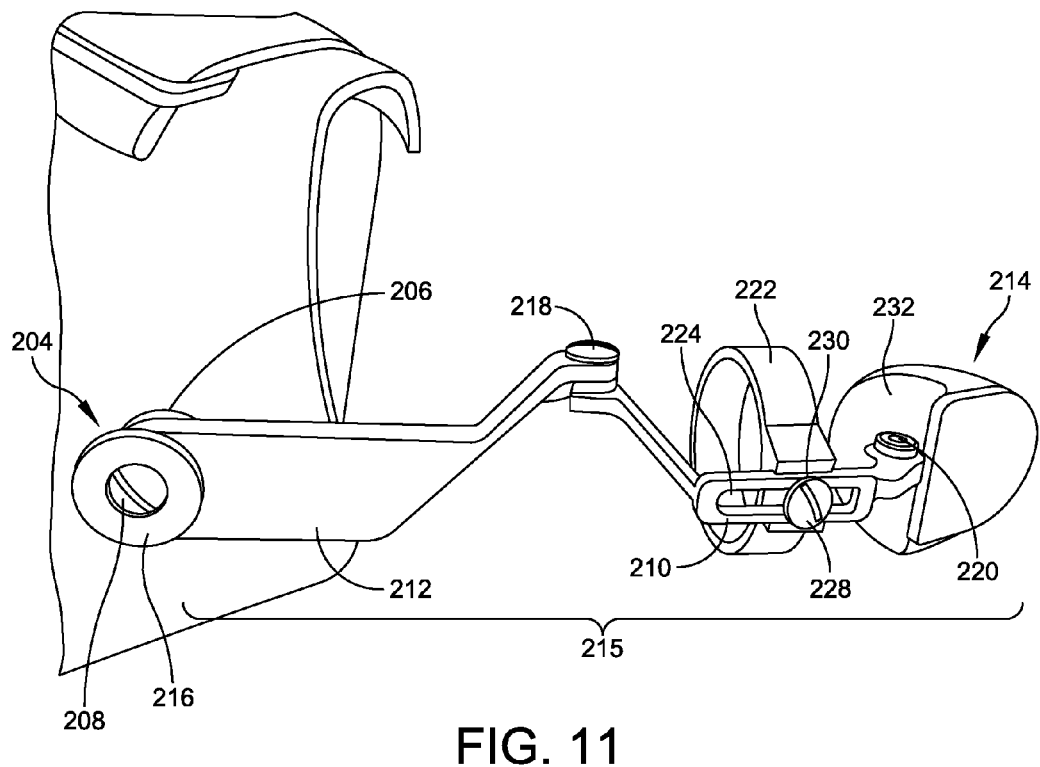
FIG. 11 illustrates a bottom perspective view of the prosthetic thumb assembly of FIG. 9.
Figure 12:
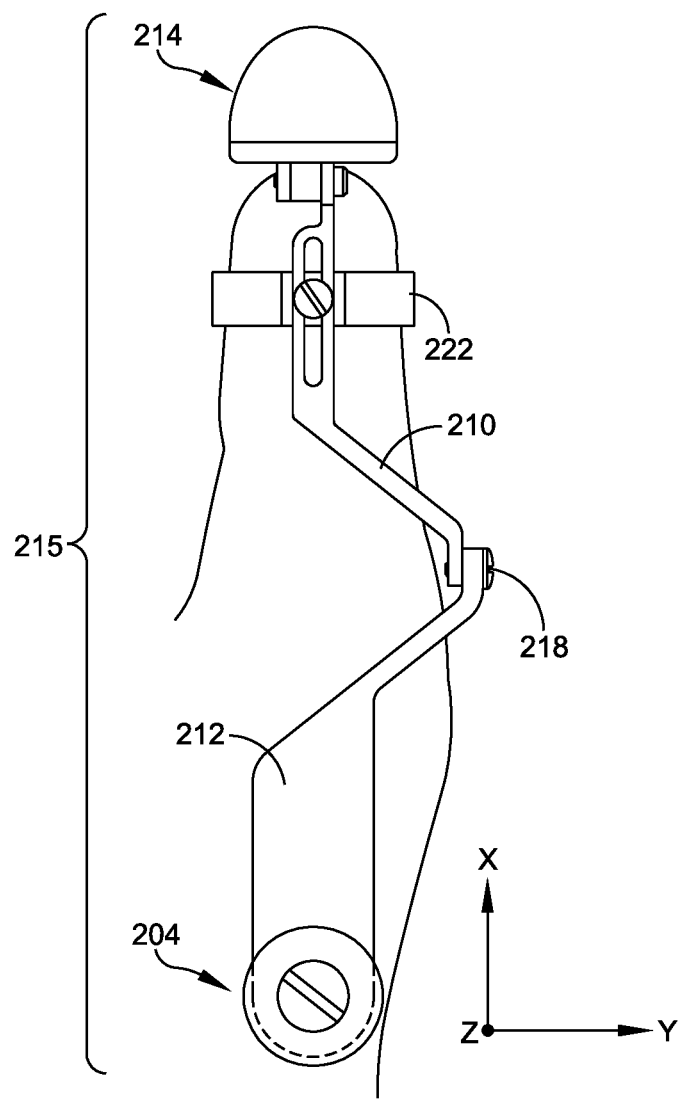
FIGS. 12-13 illustrate top views of an articulation assembly of the prosthetic thumb assembly of FIG. 9 installed upon a residual thumb and in use for adduction and abduction movements within an x-y plane, respectively.
Figure 13:
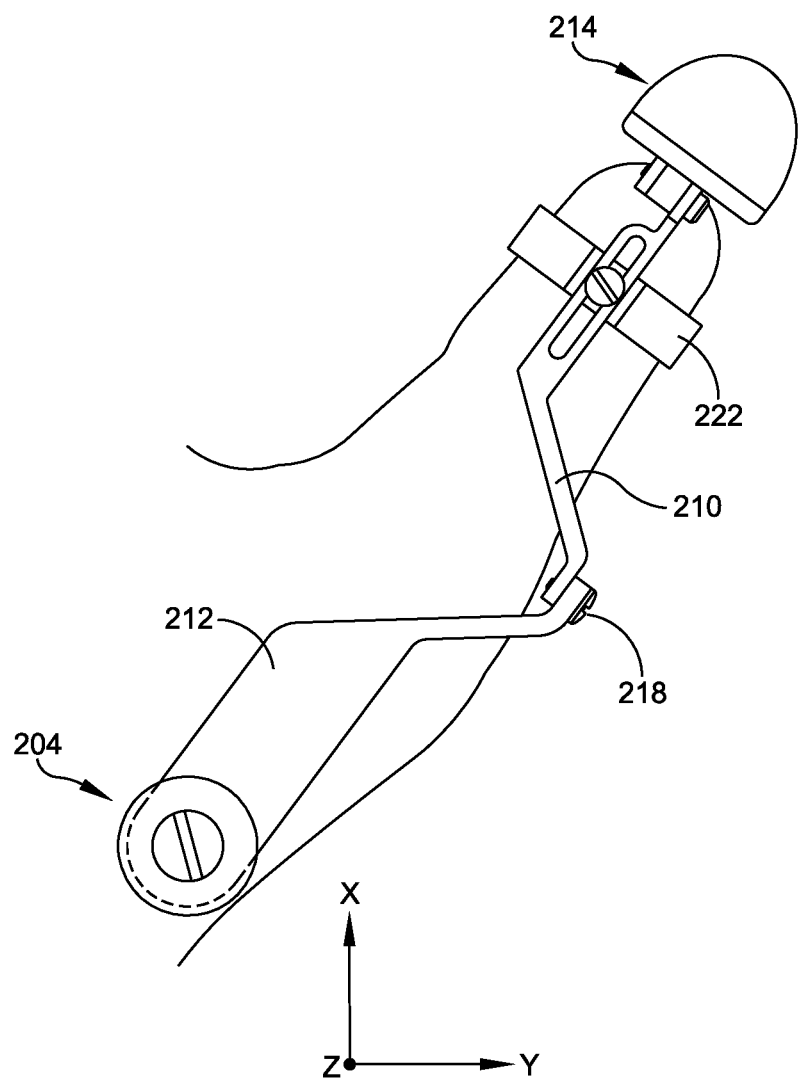
Figure 14:
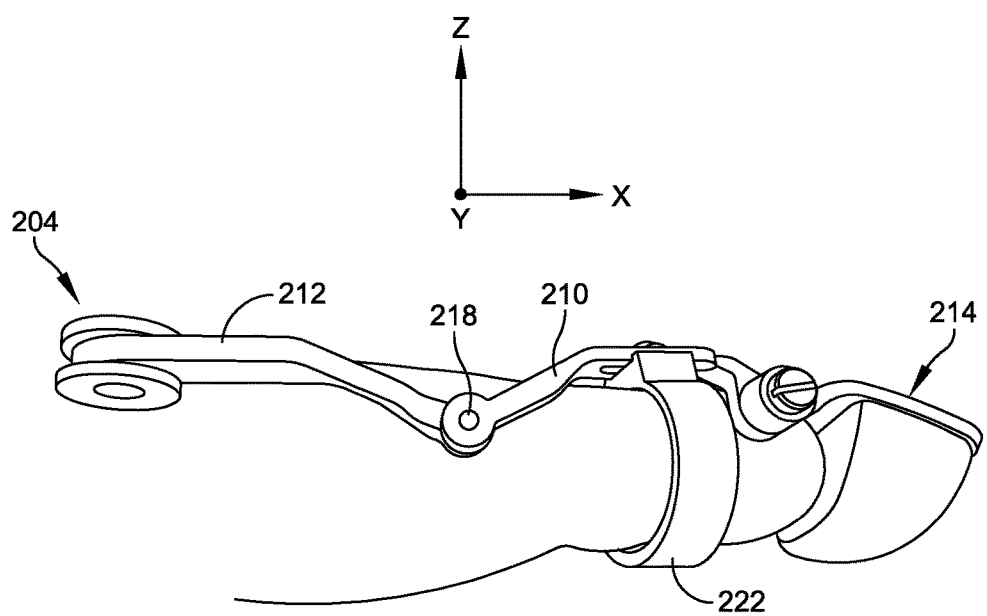
FIGS. 14-15 illustrate side views of the articulation assembly of FIGS. 12-13 installed upon a residual thumb and in use for vertical movements within an x-z plane.
Figure 15:
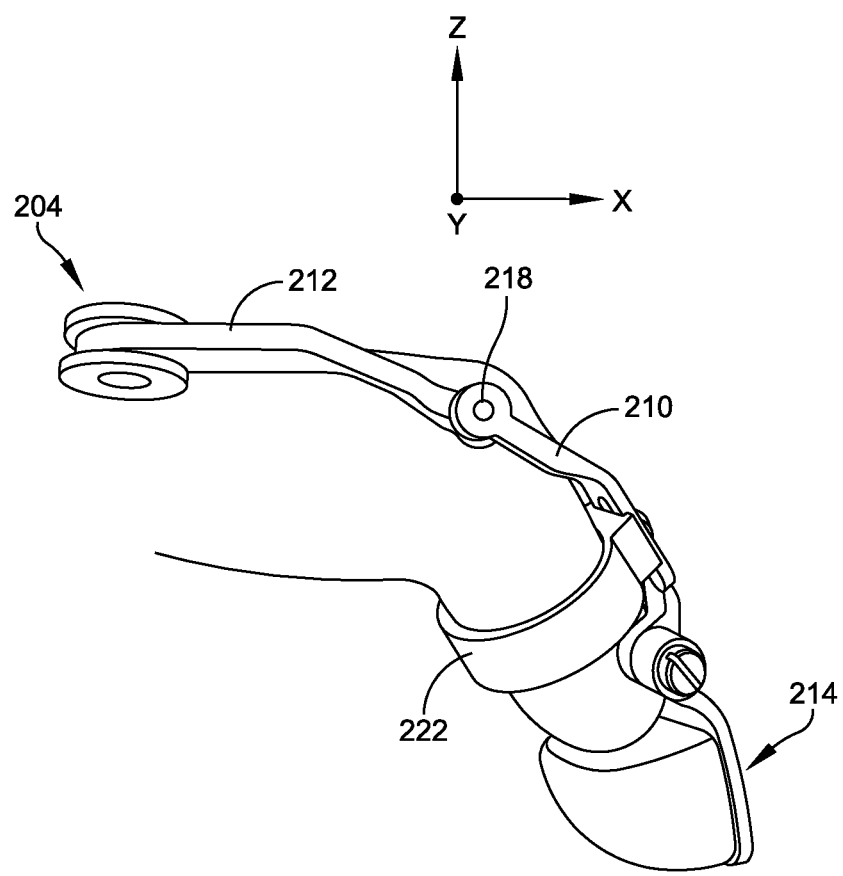

FIGS. 9-11 illustrate a number of perspective views of an alternate embodiment of a bidirectional prosthetic thumb. Embodiments of the bidirectional prosthetic thumb include an adjustable ring configured to receive and retain a user's residual thumb, along with an adjustable ring tendon, both detailed below. The ring and adjustable ring tendon allow bidirectional prosthetic thumb 200 to anchor to any length of residual thumb, including after amputation of a thumb tip or one or more thumb segments, while providing maximum fit and use flexibility, dexterity, grip, strength, and bidirectional articulation.

To facilitate an explanation of the movement of embodiments the bidirectional prosthetic thumb, relative vertical and lateral movements of the components of thumb are discussed below in relation to an x-axis, a y-axis, and a z-axis, as defined in FIG. 9.

Turning to the exemplary embodiments, FIGS. 9-11 illustrate numerous perspective views of one embodiment of a bidirectional and biomechanically driven prosthetic thumb 200, as connected with a hand strap 202. In this embodiment, prosthetic thumb 200 may include an adjustable ring tendon 210 that is rotatively coupled between a proximal anchor plate 212 at its proximal end and a coupling tip 214 at its distal end. Proximal anchor plate 212 may rotatively couple with hand strap 202 via an eccentric articulation pivot 204 that is located above the user's MCP joint when prosthetic thumb 200 is installed upon the user's residual thumb.

Articulation pivot 204 may include a strap platform 206 that is attached or affixed to hand strap 202 to provide an appropriate alignment and/or depth in relation to a remainder of prosthetic thumb 200. Articulation pivot 204 may also include an anchor-plate platform 216 that is disposed upon anchor plate 212 opposite strap platform 206, such that the proximal end of anchor plate 212 is disposed between strap platform 206 and anchor-plate platform 216, such that an articulation joint 208 may pin anchor plate 212 between anchor-plate platform 216 and strap platform 206 in a manner that rotationally couples the proximal end of anchor plate 212 to strap platform 206. In this configuration, anchor plate 212 revolves relative to strap platform 206 (and hand strap 202) about articulation joint 208, or about the z-axis in a plane parallel to the x-y plane.

Adjustable ring tendon 210 may rotatively couple with the distal end of proximal anchor plate 212 via a first hinged connection 218 and with coupling tip 214 via a second hinged connection 220. In one embodiment, a ring 222 may be disposed upon adjustable ring tendon 210. Ring 222 may be configured to concentrically receive and retain the user's residual thumb and may be formed of any appropriate metal and/or plastic material. Ring 222 may incorporate a silicone portion or portions for improved grip, comfort, and serviceability. These silicone portions may reside along a lower portion of ring 222 and/or they may be incorporated along natural pressure points between the thumb and ring 222, such as at the top of the proximal phalanx bone. Ring 222 may be one of a number of interchangeable rings, each sized to achieve an ideal fit. The rings may be provided in a fit kit (not shown) that allows the user to select the proper ring 222 to adjust for weight gain or loss, swelling, and so on.

Ring 222 may be adjusted along the length of adjustable ring tendon 210 by sliding ring 222 along a longitudinal adjustment mechanism disposed within tendon 210. In one embodiment shown in FIG. 11, the longitudinal adjustment mechanism may be a longitudinal adjustment channel 224 formed within adjustable ring tendon 210. To adjust ring 222, a user may simply slide ring 222 along a length of channel 224 before securing ring 222 via a screw 228 or any other appropriate fastener, to tendon 210 at a target location 230. Target location 230 may be based on a length of the user's residual thumb and result in an alignment of articulation pivot 204 above/over the user's MCP joint when the user's thumb is retained within ring 222. Longitudinal adjustment channel 224 may have any appropriate length along adjustable ring tendon 210. Further, the longitudinal adjustment mechanism may take any appropriate size, shape, type, and/or configuration. For example, in an alternate embodiment, the longitudinal adjustment mechanism may be formed from a number of separate longitudinal adjustment holes disposed along the length of adjustable ring tendon 210.

As shown in FIGS. 9-11 and discussed above, coupling tip 214 may rotatively couple with the distal end of adjustable ring tendon 210 via second hinged connection 220. In one embodiment, second hinged connection 220 may be a screw configured to be tightened at any desired angle such that second hinged connection 220 may be adjusted through 360 degrees of rotation, limited only by interference with the other components of prosthetic finger 200. In this regard, second hinged connection 220 offers infinite adjustment options within a full range of feasible and/or desirable fingertip angles.

Coupling tip 214 may include a tip pad 232. Tip pad 232 may be formed from a soft-textured silicone or other material that mimics the texture of a real finger. This aids with gripping and provides a softer touch. A cap may also be fitted over tip pad to further provide a realistic thumb appearance. In one embodiment, a touchscreen mechanism (not shown) may be provided to allow the user of prosthetic thumb 200 to operate capacitive touchscreens, which react to the body's natural current. The touchscreen mechanism allows the user to direct his or her body current through coupling tip 214.

As discussed above, prosthetic thumb 200 is designed for bidirectional articulation. Specifically, proximal anchor plate 212, adjustable ring tendon 210, and distal coupler 214 may together form an articulation assembly 215 that moves within two perpendicular planes. First, articulation assembly 215 rotates laterally relative to articulation pivot 204 via articulation joint 208, providing prosthetic thumb 200 with a first direction of movement about an axis parallel to the z-axis and within a plane parallel to the x-y plane. Second, first and second hinged connections 218 and 220, which rotatively couple adjustable ring tendon 210 between proximal anchor plate 212 and distal coupler 214, respectively, provide articulation assembly 215 with a second, vertical direction of movement about an axis parallel to the y-axis and within a plane parallel to the x-z plane. As a result, the user may achieve more lifelike movement of distal coupler 214 that emulates the natural articulation of a thumb by moving his or her residual thumb laterally (e.g., adducting and/or abducting the residual thumb) within ring 222 to actuate articulation assembly 215 of prosthetic thumb 200 in the first direction, and by moving his or her residual thumb vertically within ring 222 to actuate articulation assembly 215 of thumb 200 in the second direction, thereby achieving both lateral and vertical articulation of coupling tip 214.

Embodiments of prosthetic thumb 100, 200 are custom designed and individually fitted to accommodate a variety of differing user conditions. In this regard, each thumb 100, 200 may be custom manufactured to fit a particular patient or user, providing both custom functionality as well as a mechanical match to the anatomical joint articulation of the user.

To further provide better aesthetics, embodiments of prosthetic thumb 100, 200 may be coated with films and/or colorings matched to the user's skin tone. An additive manufacturing process (i.e., 3D printing) facilitates this ability to customize the intricacies of the prosthetic design in order to optimize prosthetic finger 100, 200 for each patient.

Various embodiments of thumb 100, 200 may be formed of any suitable structural material that is non-irritating to human skin and allows the user to operate the prosthetic with confidence. Exemplary materials include titanium, stainless steel, aluminum, silicone, carbon fiber, nylon, plastic, wood, rubber, gold, silver, tungsten, flex cable, neoprene, or any other suitable structural material. In one embodiment, the device may be 3D printed from Duraform EX polymer material.

Portions of embodiments of prosthetic thumb 100, 200 may be used for differing conditions of the user. Embodiments can accommodate varying levels of thumb loss, i.e., for thumb tips or full thumbs. Additionally, using biocompatible materials, various embodiments prosthetic thumb 100, 200 may be applied as an orthopedic implant that may be surgically implanted into a user's thumb. This option may be applied for users having injuries that have crushed their thumb bones without the ability to heal or be repaired. In these situations, implantable embodiments of prosthetic thumb 100, 200 are able to take the place of the user's original bones without the need for amputation.

Once thumb 100, 200 (adjusted or otherwise) is in place, the user may utilize his or her natural finger movements. The rotatively coupled components of thumb 100, 200 will articulate using the same cognitive process that was previously utilized for the original thumb.

Embodiments of thumb assembly 100, 200 described above exhibit numerous unique characteristics and provide a variety of medical benefits. An individual's unique physiology and lifestyle patterns dictate the function and performance expected of his or her hands. Using embodiments of the prosthetic thumb assembly described herein, patients may regain independent control of their hands, whether at work or at play. Each device is custom designed and manufactured for a specific individual, and incorporates features that allow for further fine-tuning and adjustment of fit to account for post-manufacturing fluctuations (e.g., shims, interchangeable rings), enabling the device to fit the user in a manner that allows for a biomechanically driven, low profile, lightweight, highly functioning return to the user's everyday activities, no matter what those activities might entail. A few examples include typing, playing the piano or another instrument, woodworking, and much more.

Embodiments of the biomechanical finger assembly described above are body powered, accommodate bidirectional movement, and feature linked components that articulate when the user simply moves his or her residual thumb. Beyond allowing for a simple, elegant, and streamlined design that offers strength in the lowest possible profile design, employing the user's own biomechanics to drive embodiments of thumb 100, 200 provides a host of medical benefits to the user, including reduced swelling of and increased circulation to the residual thumb and the hand as a whole, and supporting healthy joints in the injured thumb and adjacent fingers.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A bidirectional prosthetic thumb device, comprising:
an eccentric articulation pivot attached to a hand strap;
an articulation assembly rotatively coupled with the eccentric articulation pivot, the articulation assembly comprising:
a coupling tip;
a proximal anchor plate having a proximal end and a distal end, the proximal end rotatively coupled with the eccentric articulation pivot;
an adjustable ring tendon having a distal end and a proximal end in opposition to one another, the distal end pivotally attached to the coupling tip and the proximal end pivotally attached to the distal end of the proximal anchor plate; and
a ring configured to concentrically receive a residual thumb of a user, the ring in operable connection with the adjustable ring tendon, and selectively positionable at a target location selected from a plurality of locations between the distal end and the proximal end of the adjustable ring tendon, wherein:
the articulation pivot is configured to utilize abduction and adduction movements of the residual thumb within the ring to articulate the articulation assembly within a plane parallel to an x-y plane and about an axis parallel to a z-axis; and
the articulation assembly is configured to utilize vertical movements perpendicular to the abduction and adduction movements of the residual thumb within the ring to articulate the articulation assembly within a plane parallel to an x-z plane.

2. The bidirectional prosthetic thumb device of claim 1, wherein the hand strap is configured for attachment about a hand of the user.

3. The bidirectional prosthetic thumb device of claim 1, wherein the articulation pivot comprises:
a strap platform secured to the hand strap; and
an anchor plate platform, wherein a proximal end of the proximal anchor plate is rotatively coupled between the strap platform and the anchor plate platform via an articulation joint.

4. The bidirectional prosthetic thumb device of claim 3, wherein the articulation joint comprises one of a pin or a screw.

5. The bidirectional prosthetic thumb device of claim 1, wherein the target location of the ring along the adjustable ring tendon comprises a location that aligns the articulation pivot with a metacarpophalangeal (MCP) joint of the user when the residual thumb of the user is retained within the ring.

6. The bidirectional prosthetic thumb device of claim 1, wherein the ring comprises a select one of a number of interchangeable rings, each of the interchangeable rings having a diameter that is sized to receive a different sized residual thumb.

7. The bidirectional prosthetic thumb device of claim 1, wherein the coupling tip includes a tip pad.

\* \* \* \* \*